United States Patent [19]

Luiset

[11] Patent Number: 4,834,652
[45] Date of Patent: May 30, 1989

[54] DENTAL HANDPIECE

[75] Inventor: Jean-Jacques W. Luiset, Geneva, Switzerland

[73] Assignee: Micro-Mega (Suisse) S.A., Switzerland

[21] Appl. No.: 160,659

[22] Filed: Feb. 26, 1988

[30] Foreign Application Priority Data

Mar. 6, 1987 [CH] Switzerland ................ 859/87-9
Jan. 27, 1988 [FR] France ................ 88 00939

[51] Int. Cl.$^4$ ............................................. A61C 1/02
[52] U.S. Cl. .................................... 433/105; 453/133
[58] Field of Search ............... 433/133, 131, 130, 114, 433/105

[56] References Cited

U.S. PATENT DOCUMENTS 4,475,889 10/1984 Garcia et al. ................... 433/114

Primary Examiner—Robert Peshock
Attorney, Agent, or Firm—Kane, Dalsimer, Sullivan, Kurucz, Levy, Eisle and Richard

[57] ABSTRACT

The handpiece comprises a speed reducer (34) formed by an interchangeable modular unit. This reducer (34) is mounted in a housing (15) equipped with bearings (16, 17) supporting the input shaft (1), and the output shaft (10) respectively. The housing is closed on the input side by a side plate (18) formed from a piece which has a fixed wheel (7), is concentric with respect to the input shaft and is equipped with radial toothing (6) facing the inside of the housing (15). The output shaft (10) comprises, at its rear end, an output wheel (9) having a radial toothing (8) facing the interior of the housing. A ball thrust bearing is provided between an internal shoulder (15a) of the housing and an external shoulder (9a) of the output shaft. On an inclined cylindrical part (2) extending the input shaft (1), there is mounted, in free rotation, an intermediate wheel (3) provided on each of its faces with radial toothings (4, 5), one of which cooperates with the radial toothing of the fixed wheel (7), and the other with a radial toothing (8) of the output wheel (10). The gearing ratios are selected such that the intermediate wheel transmits a geared-down rotation to the output wheel (9).

9 Claims, 2 Drawing Sheets

DENTAL HANDPIECE

FIELD OF THE INVENTION

The invention relates to a dental handpiece according to the preamble of claim 1.

PRIOR ART

A handpiece of this type is known, for example from the applicant's French Patent FR No. 2,572,646, according to which the speed-reducing device is in the form of an interchangeable module which can be easily mounted inside the handpiece and replaced, as required, by another module of the same design which has a different speed-reducing ratio or even a speed-increasing ratio.

Developments in the art of dentistry have given rise to new requirements, in particular in the field of rotary instruments, and consequently in that of devices supporting and driving these rotary instruments. This is the case in implantology, whose development has brought about the need for handpieces capable of driving certain instruments for the operations of drilling, tapping, etc. at low speed and with considerable torque.

At present, the driving motors which are on the market have rotary speeds from 4,000 to 40,000 r.p.m., while some work, in particular implantology, requires tool speeds of the order of only 600 to 100 r.p.m., or even of 10 r.p.m. It is thus necessary to bring about a considerable reduction in speed. A first solution would reside in developing low speed motor units or geared motors, but this would result in the dentist needing to have available further ranges of handpieces and a range of motors, which would be unacceptable for him for obvious reasons of handling and cost. Another solution is to use differential reducers.

There is known, for example, in the field of handpieces, according to U.S. Pat. No. 4,306,865, a differential reducer with planet gears, in which the input shaft carries a toothed gear engaged with three planet wheels, which are themselves engaged with a fixed crown gear surrounding the assembly, the planet carrier being integrally formed with the output shaft. However, this device is relatively complicated because of the number of pieces which have to turn, and it results in reducing ratios only of the order of 10:1. By mounting several planet gears of this type one behind the other, it is possible to obtain larger reducing ratios. However, the size of the reducing ratio is proportional to the number of planet gears used, and it is therefore not possible to obtain very large reducing ratios in a small volume.

According to another French Patent No. 2,572,645, and still in the field of handpieces, a reducer module is used in order to save space, which comprises an intermediate shaft which is oblique with respect to the input and output shafts and is equipped at each end with gears engaging respectively with the input gear and the output gear. However, the reducing ratio obtained by this device is limited to the ratio of the teeth of the different cooperating gears, and it cannot therefore be very great.

In the field of general mechanics, there are known differential reducers of large reducing ratios, as described for example in U.S. Pat. No. 2,699,690. This reducer comprises an oscillating toothed wheel mounted in free rotation on an inclined portion of the input shaft and provided with toothing on each of its lateral faces, one of which cooperates with a fixed toothing, the other with the toothing of an output wheel, at least two of the cooperating toothings having a different number of teeth. This reducer is preferably provided to be applied to the driving mechanism of a blind or roller blind, and it takes up too much space to be used in dentistry, a simple homothetic reduction of the dimensions being incompatible with the strength of the gear teeth, which have a very small diametral pitch.

SUMMARY OF THE INVENTION

The object of the present invention is to provide a dental handpiece provided with a differential reducer which enables a large reduction in speed of a fixed ratio, which can be as much as approximately 2,000:1, and in which this reducer must moreover be designed in such a way that it can be constructed with different reducing ratios, can take up less space and can be of a simple design.

To this end, the dental handpiece according to the invention is defined by the defining clause of claim 1.

The modulator unit of this novel handpiece has a number of advantages. Its construction enables it to be assembled and disassembled easily, either for the purposes of maintenance or to modify the reducing ratio by exchanging reducing modules. Very large gearing reductions are achieved in a limited volume, and the number of moving parts is reduced by comparison with conventional reducers, which reduces the angular clearance. The speed of the intermediate wheel is low and will even be zero if the number of teeth in the fixed wheel and that of the cooperating face of the intermediate wheel are the same. The torque is limited by the connection of the mechanical reactions between the input shaft and the output shaft, this torque often being excessive and problematic with conventional reducing systems of very large reducing ratio.

The reducer according to the invention is suitable for application to dental instruments requiring a very slow speed, such as for example drills, screw-tapping equipment, and low-speed burs, as necessary in particular in the field of implantology.

Preferably, the housing is closed on the input side by a side plate provided by the fixed toothed wheel and the bearing of the input shaft, and the output wheel is in one piece with the output shaft.

The inclined cylindrical part is preferably extended by a pivot aligned with the input shaft and the rear part of the output shaft, situated inside the housing, is hollow and comprises a rolling bearing receiving said pivot.

Furthermore, the inclined cylindrical part is preferably housed in a needle bearing mounted between two shoulders situated on either side of the said inclined cylindrical part and the internal periphery of the intermediate wheel.

Other features result from the dependent claims.

BRIEF DESCRIPTION OF THE DRAWINGS

A preferred embodiment of the handpiece will now be described below, with the aid of the following description and the attached drawing, in which.

DESCRIPTION OF THE PREFERRED EMBODIMENT

Figure 1:
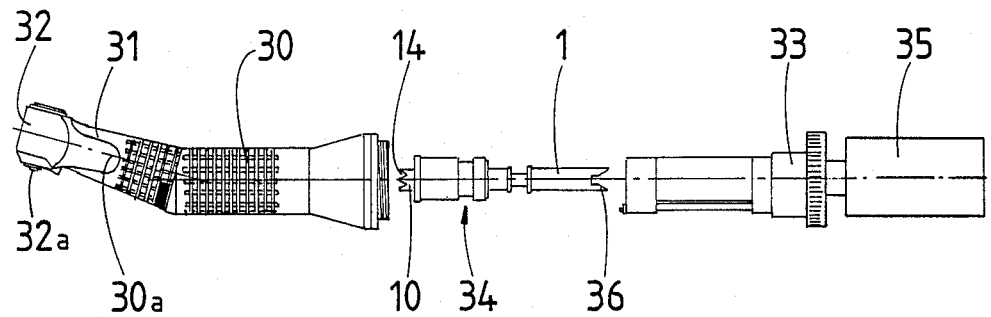
FIG. 1 is a general exploded view of the dental handpiece according to the invention.

In FIG. 1, the handpiece, which is in the form of a contra-angle, is composed in known manner of a sleeve 30, a front part 31 comprising a transmission shaft 30a which is diagrammatically illustrated by the checked area, and the head 32 which is provided with means (not shown) for fastening the tool 32a, an internal part 33 which is adjusted in the sleeve 30 and provided to be connected to a driving piece 35. To transmit the movement of the driving piece 35 to the transmission shaft 30a, there is provided a speed reducer 34, which is in the form of an interchangeable modular unit and comprises an input shaft 1 whose end is provided with a driving mechanism 36 compatible with the driving mechanism of the driving piece 35, and an output shaft 10 provided with a radial toothing 14 engaging with a toothing in the transmission shaft 30a.

Figure 2:
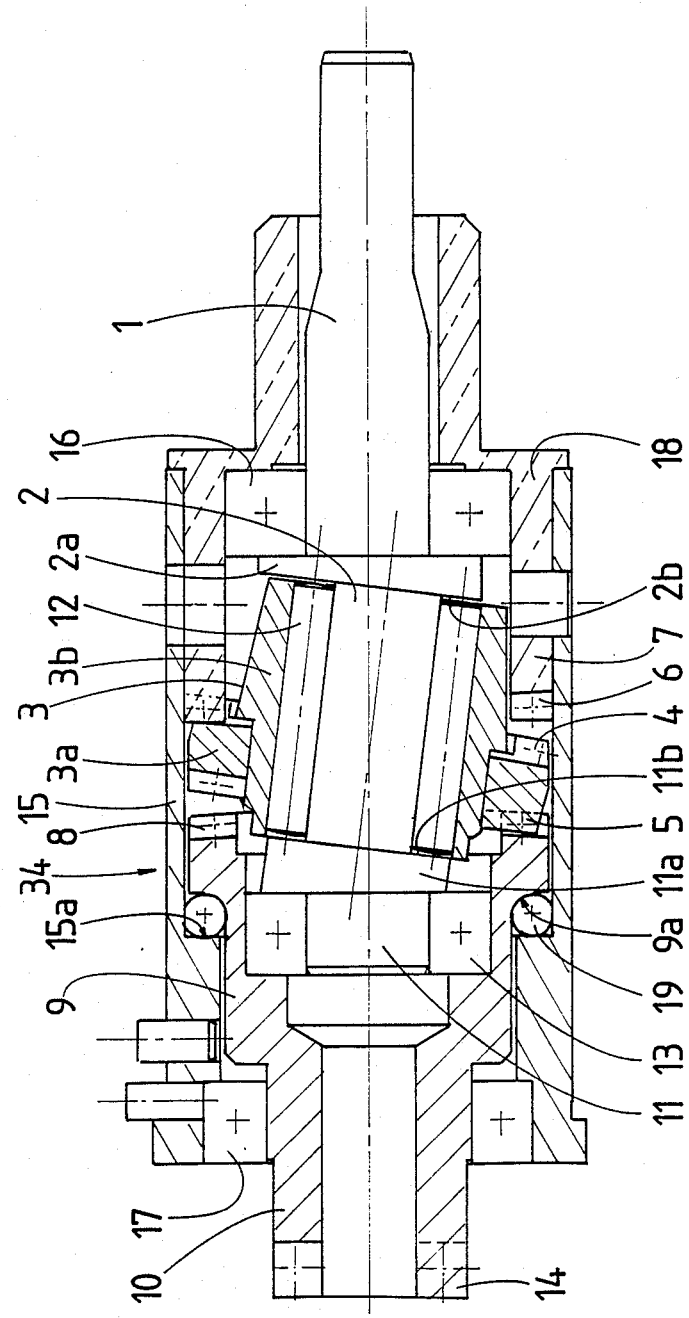
FIG. 2 represents a diagrammatic view in longitudinal section of the speed reducer.

According to FIG. 2, it can be seen that the input shaft 1 and the output shaft 10 of the reducer 34 are mounted in a housing 15 and are supported by ball bearings 16 and 17 respectively, housed in the housing 15. This housing 15 is closed on the input side by a side plate 18 in one piece with a fixed wheel 7 which is provided with a radial toothing 6 facing the inside of the housing 15 and arranged concentrically with respect to the input shaft 1. The ball bearing 16 supporting the input shaft 1 is mounted inside the side plate 18. The output shaft 10 is hollow and is in one piece, at its rear end, with an output wheel 9 which is concentric with respect to it and which has a radial toothing 8 which also faces the inside of the housing 15. On the outer periphery of the output wheel 9 there is formed a shoulder 9a which faces the output side and is arranged opposite a shoulder 15a provided on the inner periphery of the housing 15, the annular space between the shoulders being occupied by balls 19 forming a ball thrust bearing with these shoulders 9a and 15a.

The input shaft 1 is extended by a cylindrical part 2 which is inclined with respect to it and separated from it by means of a collar 2a which forms the shoulder 2b. The face of this shoulder 2b facing the inside of the housing has, with respect to a plane perpendicular to the input shaft, the same inclination as the cylindrical part 2 with respect to this input shaft 1. This angle of inclination is very small, of the order of 5° to 15°.

The inclined cylindrical part 2 is extended by a pivot 11 aligned with the input shaft 1, a collar 11a separating the two parts and forming the shoulder 11b. The face of this shoulder 11b facing the inside of the housing 15 has, with respect to a plane perpendicular to the input shaft, the same angle of inclination as the shoulder 2b. The rear part of the output shaft 10 is hollow and receives a bearing 13, formed by ball bearings, in which there is located the pivot 11 in order to ensure the centering of the input shaft 1.

On the inclined cylindrical part 2 of the input shaft 1 there is mounted in free rotation an intermediate wheel 3 provided on its two faces with annular engaging zones formed by radial toothings 4, 5. A needle bearing 12 located between the inclined cylindrical part 2 and the internal periphery of the intermediate wheel 3 is held between the two shoulders 2b and 11b, and ensures trouble-free rotation of the intermediate wheel 3 on the inclined part 2. On the face of the intermediate wheel 3 facing the input shaft 1, the radial toothing 4 has the number of teeth $Z_2$ and, on the other face, the radial toothing 5 has the number of teeth $Z_3$. The intermediate wheel 3 cooperates by means of its radial toothing 4 with the toothing 6, which has the number of teeth $Z_1$, of the fixed wheel 7 arranged concentrically with respect to the input shaft 1, while the radial toothing 5 cooperates with its other face with the radial toothing 8, which has the number of teeth $Z_4$, of the output wheel 9.

According to a preferred form of the invention, the intermediate wheel 3 is in two parts, one part 3a supporting the two radial toothings 4, 5 and connected to a part 3b mounted on the needle bearing 12. The part 3a supporting the radial toothings is constructed as a function of the reducing radio sought and is thus different from one reducer to the next.

To cause the wheels to move, it is first ensured that the toothing 4 of the intermediate wheel 3 only engages the toothing 6 of the fixed wheel 7 over a limited zone of a few teeth, while the other toothing 5 of the intermediate wheel 3 only engages the toothing 8 of the output wheel 9 over a zone which is also limited to a few teeth and is diametrically opposite.

If the input shaft 1 and thus the inclined part 2 make a complete turn, the latter describes in space two cones of opposite vertex, and by this movement drives the intermediate wheel 3 which is mounted freely on this inclined part 2. During this movement, the zones of contact between the intermediate wheel 3 and the fixed wheel 7 on the one hand, and the output wheel 9 on the other hand, circulate along corresponding toothings. This movement of the intermediate wheel 3 is a type of vacillating movement. The very small angle of inclination, from 5° to 15°, of the inclined part 2 and thus of the intermediate wheel 3 ensures a movement over a minimum of three teeth at each engagement.

It can easily be deduced from the above that the ratio between the speed of rotation n1 of the input shaft 1 and the speed of rotation n2 of the output shaft 2 is given by the formula:

$$n2/n1 = 1 - Z_1Z_3/Z_2Z_4$$

From this formula it can clearly be seen that the fraction must not be equal to 1, and thus the ratio $Z_3/Z_4$ must not be the inverse of the ratio $Z_1/Z_2$, since in this case the output wheel 9 remains stationary. From this formula the direction of rotation of the wheels can also be seen, that is that if the ratio $Z_1Z_3/Z_2Z_4$ is less than 1, the output wheel 9 turns in the same direction as the input shaft 1; if this ratio is greater than 1 its direction of rotation is in opposition to that of the input shaft 1.

There also results from this formula that, in order to arrive at a very large speed reduction, the ratio $Z_1/Z_2$ must be chosen very slightly less than 1 and the ratio $Z_3/Z_4$ very slightly greater than 1 (or vice versa) but slightly different.

In order to use the conception of the invention in an optimum manner in order to arrive at a very great speed reduction, the numbers of teeth are preferably chosen in the following manner:

$$Z_2 = Z_4 = N, \; Z_1 = N-1, \; Z_3 = N+1$$

According to the formula $n2/n1 = 1/N^2$, this gives the direction of rotation of the output shaft 10 as the same as that of the input shaft 1. By choosing, for example, the number N as 30, there results a speed ratio of $n2/n1$ = 1/900. By choosing N as 40, the speed-reducing ratio is 1/1,600.

By choosing the ratios of the teeth in a suitable manner, with a sufficient engagement of the teeth, there can be achieved reducing ratios chosen within a very large range. For example, if $Z_4=31$, $Z_3=32$, $Z_2=20$ and $Z_1=19$, a speed-reducing ratio of $1:5/^2/_3$ is achieved.

A single-action design can be achieved if, where $Z_3=Z_4$, the final ratio will be $1-Z_1/Z_2$, or where $Z_1=Z_2$ the ratio will be $1-Z_3/Z_4$.

The advantage of this device is that there is only a slow rotation of the intermediate wheel 3 and that the number of moving parts is very reduced with respect to the number of parts comprising the hitherto known reducers. Furthermore, because the inclined part 2 has a very small angle of inclination with respect to the input shaft 1, it can be considered that the intermediate wheel 3 occupies a limited space, almost aligned with the space occupied by the fixed and mobile wheels respectively, it being possible for the three wheels to be inserted without difficulty into a cylindrical space. As a result of the connection of the mechanical reactions between the input shaft and the output shaft, the torque is considerably limited.

Because it takes up little space and because it is in the form of a compact module, the reducer which has just been described can advantageously be used in the dental instruments necessitating a large speed reduction, it being possible for the cylindrical module to be easily inserted in the handle section of a right-handed handpiece, or in a contra-angle or even in the motor. Such a reducer can be used in particular, for example, in a drill, in a screw-tapping device, or in a low-speed bur. Of course, other applications could be envisaged without departing from the scope of the invention.

I claim:

1. A dental handpiece, in particular a contra-angle, comprising a sleeve (30) in which there is located a speed reducer in the form of an interchangeable modular unit (34) comprising an input shaft (1) and an output shaft (10) which are aligned, and a front part (31) connected to the sleeve (30) and comprising a transmission shaft (30a) and means (32a) for fastening the tool, the rear end of the input shaft (1) being intended to be coupled to a driving piece (35), wherein the modular unit (34) comprises a housing (15) in which there are located bearings (16, 17), preferably ball bearings, for the input shaft (1) and output shaft (10), and of which the input side is provided with a fixed wheel (7) arranged concentrically with respect to the input shaft (1) and provided with a radial toothing (6) facing the interior of the housing, and wherein the output shaft (10) comprises at its rear end an output wheel (9) having a radial toothing (8) facing the inside of the housing and, on its external periphery, a shoulder (9a) facing the output and arranged opposite a shoulder (15a) provided on the periphery of the housing, the annular space between the shoulders being occupied by balls forming with these shoulders (9a, 15a) a ball thrust bearing, and wherein the input shaft (1) is extended by a cylindrical part (2) inclined with respect to this input shaft (1) and on which there is mounted in free rotation an intermediate wheel (3) provided on each of its faces with radial toothings (4, 5), one of which cooperates with the toothing (6) of the fixed wheel (7) and the other with the toothing (8) of the output wheel (9), the ratio between the number of teeth of at least two cooperating toothings being not equal to one and different from the ratio between the number of teeth of the two other toothings, so that when input shaft (1) rotates, the intermediate wheel (3) executes vacillating rotary movement freely on cylindrical part (2) as a result of the engagement of toothing (4) with some of the toothing (6) and toothing (5) with some of the toothing (8) to thereby transmit a geared down rotation to output shaft (10).

2. A handpiece as claimed in claim 1, wherein the housing (15) is closed on the input side by a side plate (18) provided by the fixed wheel (7) and its toothing (6) and the bearing (16) of the input shaft (1), and wherein the output wheel (9) is in one piece with the output shaft (10).

3. A handpiece as claimed in one of claims 1 or 2, wherein the inclined cylindrical part (2) is extended by a pivot (11) aligned with the said input shaft (1) and wherein the rear part of the output shaft (10), situated inside the housing (15), is hollow and comprises a rolling bearing (13), preferably a ball bearing, receiving the said pivot (11).

4. A handpiece as claimed in claim 1 wherein the inclined cylindrical part (2) is housed in a needle bearing (12) mounted between two shoulders (2b, 11b) situated on either side of the said inclined cylindrical part, and the internal periphery of the intermediate wheel (3).

5. A handpiece as claimed in claim 3 wherein the inclined cylindrical part (2) and the pivot (11) form a single piece with the input sahft (1), and wherein the said inclined cylindrical part is situated between two collars (2a, 11a) which connect it on one side to the input shaft (1) and on the other side to the pivot (11), and whose faces facing the cylindrical part have the same angle of inclination and make up the said shoulders.

6. A handpiece as claimed in claim 1, wherein the intermediate wheel (3) is made up of a part (3a) supporting the two radial toothings (4, 5), and connected to a part (3b) mounted on the said needle bearing (12) and which can be replaced as a function of the reducing ratio sought.

7. A handpiece as claimed in claim 1 wherein the angle of inclination of the intermediate wheel (3) is between 5° and 15°, such that it is ensured that at least three teeth always assure movement at each engagement.

8. A handpiece as claimed in claim 1 wherein the input shaft (1) is provided with a driving mechanism (36) compatible with the conventional motor driving mechanisms (35).

9. A handpiece as claimed in claim 1 wherein the output shaft (10) is provided with a radial toothing (14) engaging with the means of transmission of movement towards the head (32) of the handpiece.

* * * * *